United States Patent
Zhao et al.

(10) Patent No.: US 6,681,549 B1
(45) Date of Patent: Jan. 27, 2004

(54) METHOD AND SYSTEM WITH ELECTRONIC CONTROL DEVICES FOR BLENDING OF CHINESE MEDICINE

(75) Inventors: Xinxian Zhao, Shenzhen (CN); Pinglong Wu, Shenzhen (CN); Jinlong Huang, Shenzhen (CN); Yingping Liu, Shenzhen (CN)

(73) Assignee: Shenzhen 999 Pharmaceutical Co., Ltd., Cuangdong (CN)

( * ) Notice: Subject to any disclaimer, the term of this patent is extended or adjusted under 35 U.S.C. 154(b) by 0 days.

(21) Appl. No.: 09/857,900

(22) PCT Filed: Oct. 26, 1999

(86) PCT No.: PCT/CN99/00169

§ 371 (c)(1), (2), (4) Date: Sep. 25, 2001

(87) PCT Pub. No.: WO00/35754

PCT Pub. Date: Jun. 22, 2000

(30) Foreign Application Priority Data

Dec. 14, 1998 (CN) .......................... 98123341 A
Sep. 24, 1999 (CN) .......................... 99117111 A

(51) Int. Cl.⁷ .............................................. B65B 35/30
(52) U.S. Cl. ........................... 53/443; 53/445; 53/475; 53/502
(58) Field of Search .................... 53/474, 442.5, 53/502, 141, 493, 237, 221, 222

(56) References Cited

U.S. PATENT DOCUMENTS

| | | | | |
|---|---|---|---|---|
| 5,097,652 A | * | 3/1992 | Inamura et al. ............... 53/493 |
| 5,208,762 A | * | 5/1993 | Charhut et al. .............. 700/216 |
| 5,852,911 A | * | 12/1998 | Yuyama et al. ............... 53/168 |
| 5,946,883 A | * | 9/1999 | Yuyama et al. ............... 53/154 |
| 5,971,593 A | * | 10/1999 | McGrady ..................... 700/233 |
| 6,175,779 B1 | * | 1/2001 | Barrett ....................... 700/242 |
| 6,230,927 B1 | * | 5/2001 | Schoonen et al. ............. 221/10 |
| 6,256,967 B1 | * | 7/2001 | Hebron et al. ................ 53/501 |
| 6,318,051 B1 | * | 11/2001 | Preiss .......................... 53/493 |
| 6,364,517 B1 | * | 4/2002 | Yuyama et al. ............. 700/231 |
| 6,370,841 B1 | * | 4/2002 | Chudy et al. ................. 53/411 |
| 6,393,339 B1 | * | 5/2002 | Yeadon ...................... 700/237 |
| 6,449,927 B2 | * | 9/2002 | Hebron et al. ................ 53/501 |

\* cited by examiner

Primary Examiner—Rinaldi I. Rada
Assistant Examiner—Hemant M. Desai
(74) Attorney, Agent, or Firm—Larson & Taylor PLC

(57) ABSTRACT

The present invention relates to a method and a system with electronic control devices for blending of Chinese herbal medicine. The system includes a container consisting of a multiplicity of cases having units for storing a series of bags packed with specified concentrated medicinal herbal particles; a taking device for getting certain amount of the said bags from the specified units according to the computer instruction; a guide device for guiding the bags to the conveyor belt; a warning and pilot device for warning of running short and wrong filling the medicine. With such kind of method and system, the packed Chinese herbal medicine can be offered easy for carrying and convenient for serving. With the warning and pilot device, missing or wrong-filling of medicine can be avoided, and the reliability and safety are greatly improved.

40 Claims, 11 Drawing Sheets

METHOD AND SYSTEM WITH ELECTRONIC CONTROL DEVICES FOR BLENDING OF CHINESE MEDICINE

BACKGROUND OF THE INVENTION

The present invention relates to distributing and packing technique, particularly to the automatization application in the field of the Chinese herbal medicine. More particularly, it relates to method involving storing in packet, measuring, fetching and packing etc. for Chinese herbal medicine and the system with electronic control device for blending of Chinese herbal medicine using above methods.

Compared with the Western medicine, the Chinese herbal medicine has less the side effect and does not easily form drug resistance and can cure diseases from symptom and origin. In a wide range of the world, the vegetable drug representing by the Chinese herbal medicine has been highly regarded. But the disadvantage of Chinese herbal medicine is the fact that the preparation is much difficult. Though the prepared Chinese herbal medicine can solve the difficulty in some way, the fixed prescription is not so easy to exert the treatment effect in which the Chinese herbal medicine is quite different in curing different patient.

If each kind of Chinese herbal medicine can be distilled into effective ingredients, cranked out as the Chinese herbal medicine condensed granules and packed in certain quantity package, it will solve the problem in transportation, storage and human resources wasting and simplify the procedure of medicine taking or decocting. The patients can mix and take the medicine according to the doctor's prescription. In a traditional Chinese herbal medicine drugstore, every sort of Chinese herbal medicine has to be searched and weighed. It leads to be inaccurate and the patients need to queue up for the medicine. The mode of the Chinese herbal medicine management restricts the improvement of the overall control level of the hospital.

SUMMARY OF THE INVENTION

One objective of the present invention is to provide an electrical method for Chinese herbal medicine allotment, to overcome the disadvantages of inaccuracy, time consuming in making up the Chinese herbal medicine, uneasiness in taking and carrying the medicine and to realize the automation in the entire process from dosage to packing and offering the medicine by the help of computer programming.

Another objective of the present invention is to provide an electrical allotting system for Chinese herbal medicine, which may replace the traditional Chinese herbal medicine drugstore. Furthermore, it can enhance the efficiency by saving time and labor while being suitable for medicine carrying and taking. Particularly speaking, the present invention is a way of medicine fetching, orienting, and transporting, packing, and offering alarm signal if medicine bags have been used out completely or misplaced on the basis of the Chinese herbal medicine bag with condensed granule inside.

The objective of the present invention can be realized by constructing an method with electronic control device for blending of Chinese herbal medicine including the following steps: processing the Chinese herbal medicine into condensed granule and encapsulating those as a bunch of bags in certain quantity; placing bunches of bags provided with certain Chinese herbal medicine in predetermined quantity into respective storage units; when preparing medicine, taking out a number of medicine bags from a storage unit selected by control system based on prescription; fetching the stipulated quantity of medicine bags from the storage unit and separating the medicine bags from the bunch of the bags by medicine fetching means; carrying them to the predetermined place by transport means and packing them accordingly by packing means.

In the said method according to the present invention, the said packing step includes the following steps: delivering the medicine into the final gathering means after prepackaging by the packing means; delivering the medicine to the labeling means after packing with the final gathering means; delivering them to the exit after labeling the instruction by the labeling means.

In the said method according to the present invention, the said step for fetching and separating includes the following steps: fetching the certain quantity of medicine bags by the respective fetching means in storage units selected simultaneously and transport them to the transmission means.

In the said method according to the present invention, the said step for fetching and separating includes the following steps: fetching the scheduled quantity of medicine bags from storage units by fetching means sequentially and transport them to the transmission means.

In the said method according to the present invention, the said method further includes the following step: checking whether enough quantity of medicine bags have been stored in the storage unit whenever fetching the certain quantity of medicine bags and producing alarm signal if inadequate.

In the said method according to the present invention, the said method further includes the following steps: checking whether the medicine bags being put into the storage unit are the same as the specified variety of the medicine bags and producing alarm signal if incompatible with the specified medicine.

Another objective of the present invention can be realized by constructing an system with electronic control device for blending of Chinese herbal medicine of the Chinese herbal medicine, which includes control system, one or more medicine-containers consisting of a number of storage units for storing different sorts of Chinese herbal medicines and fetching means used for fetching certain quantity of medicine bags from storage unit and putting them onto conveyer belt.

In the system with electronic control device for blending of Chinese herbal medicine according to the present invention, the said system includes a guiding means which is used for fetching the medicine and puts them onto the conveyer belt, an alarm means used for identifying and warning if certain medicine bags run down or misplaced, a checking system used for counting the quantity of the medicine fetched out, a packing means used for packing the medicine bags checked, a final gathering means used for packing medicine bags packed and a labeling means used for printing label on medicine bags packed.

In the system with electronic control device for blending of Chinese herbal medicine according to the present invention, the said fetching means comprises a means used for separating certain quantity of medicine bags from a series of medicine bags in each storage unit by the use of the speed difference of bags in the conveyer and the intensity difference between the joint of the medicine bags and the non joint.

In the system with electronic control device for blending of Chinese herbal medicine according to the present invention, the said fetching means comprises the paired input wheels and paired output wheels of the medicine bag, the conveying belt between the both pairs for conveying the medicine bags along movement direction of bags, the length between input and the output wheels is equal to length a of the medicine bags, the rotate speed of the said input wheels is slower than the rotate speed of the output wheels.

In the system with electronic control device for blending of Chinese herbal medicine according to the present invention, the said fetching means comprises four axes, four wheels that are fixed on the said four axes. The said four axes are connected between high and low supporting plates through the bearings. Whenever the said axes rotate in one direction, it will drive a wheel move in the same direction. At the same time, another wheel on same axis is driven. The wheel will drive another wheel by the strap. The wheel will drive the wheel on the same axis. The wheel will drive wheel forward in the direction of the arrow. The said axis has two wheel drums. On the wheel drum, the drug bags are clamped through the knurl. The bolt forces against the bearing through the spring. Consequently the wheel drum can force against the side of the drug bags, the said fetching means further includes strap which functions as guiding for the drug bag. The said axis are provided with rubber ring to help bringing in the drug bags and splitting the chain of the drug bags.

In the system with electronic control device for blending of Chinese herbal medicine according to the present invention, the said fetching means comprises two toothed wheels moving in the opposite direction and the said two toothed wheels can deliver one pack of drug whenever they turn into another angle. Then the medicine fetching means can deliver certain quantity of the drugs by controlling the rotating angle of the gears.

In the system with electronic control device for blending of Chinese herbal medicine according to the present invention, the said fetching means comprises the first valve, the second valve, and control system. The said control system controls that said first valve will open and deliver certain quantity of drug bags and close itself. In the end, the second valve will be opened and drugs are fetched.

In the system with electronic control device for blending of Chinese herbal medicine according to the present invention, the said fetching means includes the slide framework of the cam connecting rod with two cams and one slide rod, the cover which can be pushed open by the driving strap of the slide rod and the drug bucket which the its opening and closing can be controlled by the said cover.

In the system with electronic control device for blending of Chinese herbal medicine according to the present invention, every storage unit consists of one fetching means. Every fetching means in each unit is provided with a guiding means, which is used as conveying the drug bags onto the conveying strap.

In the system with electronic control device for blending of Chinese herbal medicine according to the present invention, all of the storage units share one fetching means. The medicine container further comprises a servomechanism that can drive the said fetching means moving to any storage unit predetermined along guide track according to the instruction from computer.

In the system with electronic control device for blending of Chinese herbal medicine according to the present invention, the said guide track can be the upside or downside guide track. The said servo mechanism comprises a vertical guide track which can shift horizontally along the upside or downside guide track. The said fetching means can move up and down along the said vertical guide track.

In the system with electronic control device for blending of Chinese herbal medicine according to the present invention, the said servo mechanism comprises the means which can drive the said fetching means advance and retreat in a Z direction and pull out the drug bags from the storage unit.

In the system with electronic control device for blending of Chinese herbal medicine according to the present invention, the said guiding means is installed on the said fetching means shared and the said guiding means is made up of the vertical frame with a placket and the antileak patch with a bit superposition on the two sides of the placket. The said fetching means move up and down along the two sides of the antileak patch so as to fetch the drug bags and drop down on the conveying strap.

In the system with electronic control device for blending of Chinese herbal medicine according to the present invention, the said guiding means includes the upright supply bucket with a side channel on the side of the medicine fetching means shared, the transport groove between the bottom of the said fetching means and the supply bucket. From the connection of the supply bucket to the placket of the said upright supply bucket, there is a antileak patch which can move up and down along with the transport groove for protecting the leaking of the drug from the opening of the supply bucket.

In the system with electronic control device for blending of Chinese herbal medicine according to the present invention, the said guiding means can be a small box that is connected with the said fetching means. Every pack of the drug is delivered to the small box and the medicine fetching means will deliver the said small box to the exit of the tank after fetching one set pack of the medicine.

In the system with electronic control device for blending of Chinese herbal medicine according to the present invention, the said alarm means includes the bar-code reader, the signal lamp on every unit of the medicine container. The signal lamp will light after the drugs runs out of stock. The bar-code reader will read the bar code on the drug box when append drugs. The said signal lamp will flicker if the drugs are same as medicine in the unit. After the drugs are loaded, it begins to read the bar code again. If the drugs are loaded correctly, the signal lamp will turn off.

In the system with electronic control device for blending of Chinese herbal medicine according to the present invention, the said alarm means comprises the bar-code reader, the indicator means. After the drugs in certain unit have been fetched out, the indicator means can display the drug's name and place. When loading the drug, the bar-code reader will read the bar code on the drug box and detect if the medicine is the right drug.

In the system with electronic control device for blending of Chinese herbal medicine according to the present invention, the transmission means includes the horizontal transmission strap, worktable, lifting strap connected between the end of the horizontal transmission strap and the worktable. The lifting strap has baffle plates on both sides of the transmission strap.

In the system with electronic control device for blending of Chinese herbal medicine according to the present invention, a guiding patch is installed between the horizontal transmission strap and the lifting strap.

In the system with electronic control device for blending of Chinese herbal medicine according to the present invention, the said control system determines the medicine containers and the location of the storage unit where drug bags are taken according to the prescription.

In the embodiment of the Method and system with electronic control device for blending of Chinese herbal medicine in according to the present invention, different kinds of the condensed granule of the Chinese herbal medicines in various kind of packing can be presorted in one or more medicine containers comprising a number of storage units. The computer will determine to fetch out certain quantity of Chinese herbal medicine bags from which storage unit of which medicine containers according to the prescription, and offer them to different patients for their easy carrying and taking after picking up enough quantity and being packed. Because a servo mechanism and a guide means have been installed in the system according to the present invention. It can either ensure to fetch the medicine fast enough and to deliver in a safe way. It also ensure the curative effect and does not need to keep the patients waiting. It can save time for the patients who need to wait a long time in getting the traditional Chinese herbal medicine. In that way, the hospital can reduce the space of the drugstore; improve the working condition in drugstore and save time for the druggists. At the same time, it can prevent getting the wrong medicine or providing the wrong prescription so as to improve the safety.

BRIEF DESCRIPTION OF THE DRAWINGS

The invention will now be described in more detail by way example with reference to accompanying drawings in which.

DESCRIPTION OF THE PREFERRED EMBODIMENTS

1. Packing Form for Single Medicine

In the system of the present invention, various kinds of packing shapes for one sort of the Chinese herbal medicine (condensed granule) can be adopted in order to meet the different kind of packing requirement in the embodiment so as to prepare for the medicine automatically. Firstly, various kinds of packing shapes are shown as follow:

1.1) A-A type

Figure 1:
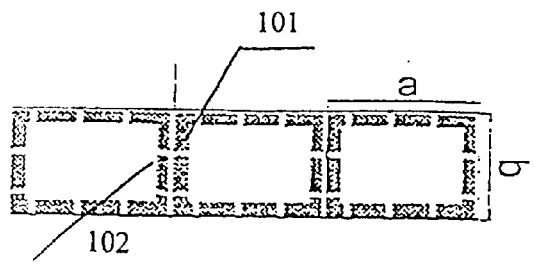
FIG. 1 shows a form of the medicine packet used in the present invention.
Figure 2:
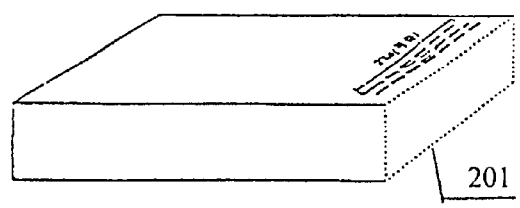
FIG. 2 is a structural view of the packet shown in FIG. 1.

As shown in FIG. 1, A-A type means that all same sizes of the drug bags, such as length a or width b, are lined up for packing one by one in turn along the length direction. Between the medicine bags, there is a breakable juncture. In FIG. 1, the shadow part 101 is the pressing seal. The intensity of the cutting line 102 is the lowest and it can be pulled apart when being pulled. In practical use, two or three packs of the drug bags can be folded in a line as the box of the FIG. 2. The broken line 201 in the front part of the box is used as cutting line. It can be torn off when loading medicine so that the inner medicine bags can be taken out continuously.

1.2) A-B type

Figure 3:
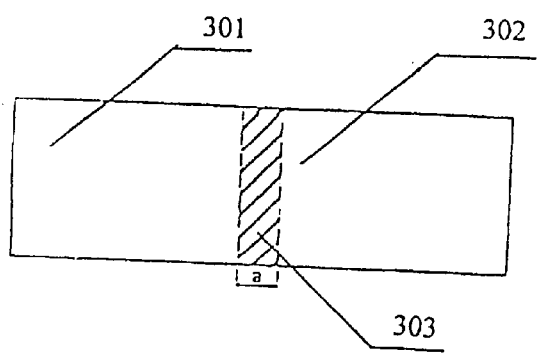
FIG. 3 is a structural view of another packing form in the present invention.
Figure 4:
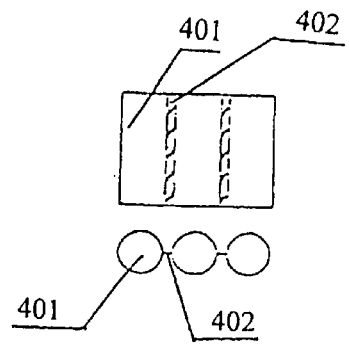
FIG. 4 is a structural view of an example in the packing shape of the FIG. 3.
Figure 5:
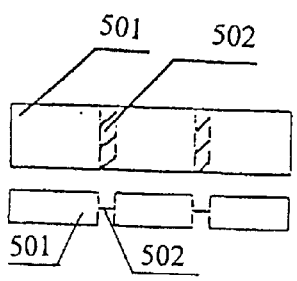
FIG. 5 is the structural view of another example in the FIG. 3.

As shown in the FIG. 3, the packages 301 and 302 can be forms of drug bag. The connecting section 303 between the two bags is shown as the shadow. In this place, the connecting section may not be a straight line and its frame depends on the size of the shape of the medicine-packing bag. In this frame, the packages 301 and 302 can be random shape such as two or more packages in cylinder form shown in FIG. 4. Here, the medicine bags 401 displays in a shape of cylinder. Between the cylindrical medicine bags, it is the connection 402 which can be pulled apart. The package of Type A-B can also be the breakable connection 502 of the two or more rectangle package 501 as shown in FIG. 5.

1.3) A-C Type

Figure 6:
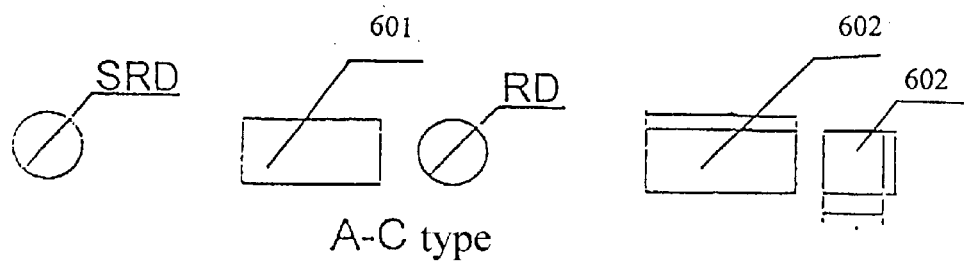
FIG. 6 is the structural view of the third packing shape in the invention.

As shown in FIG. 6, A-C type means any column or square shapes in bulk and not be connected each other. The figure shows the cylindrical package 601 and rectangle package 602 respectively.

2. The Basic Structure of System in the Present Invention

Based on the electrical allotment method and system of the present invention, it is desired to adopt the smallest quantity as basic packing unit (supposed as a gram) for each drug. According to respective dose of each drug in the prescription, the number of package in the said suitable quantity can be determines. In other words, each kind of the medicine can be composed by a number of the basic packing units in each pack of medicine.

The following is the assumption of a prescription:

Name: Zhang San Sex: male Age: 35

Drug and Dose

Pseudo-ginseng . . . 3aX3

Ginseng . . . 5aX3

Malt . . . 8aX3

In this drug, there are 9 bags of pseudo-ginseng, 15 bags of ginseng and 24 bags of malt. The doctor can input the prescription data into a computer. The allotment system for the Chinese herbal medicine according to the present invention can take out and pack 9 bags of pseudo-ginseng, 15 bags of ginseng and 24 bags of malt automatically. At the same time, it will print out the medicine taking instruction and hand over to the patients.

Figure 7:
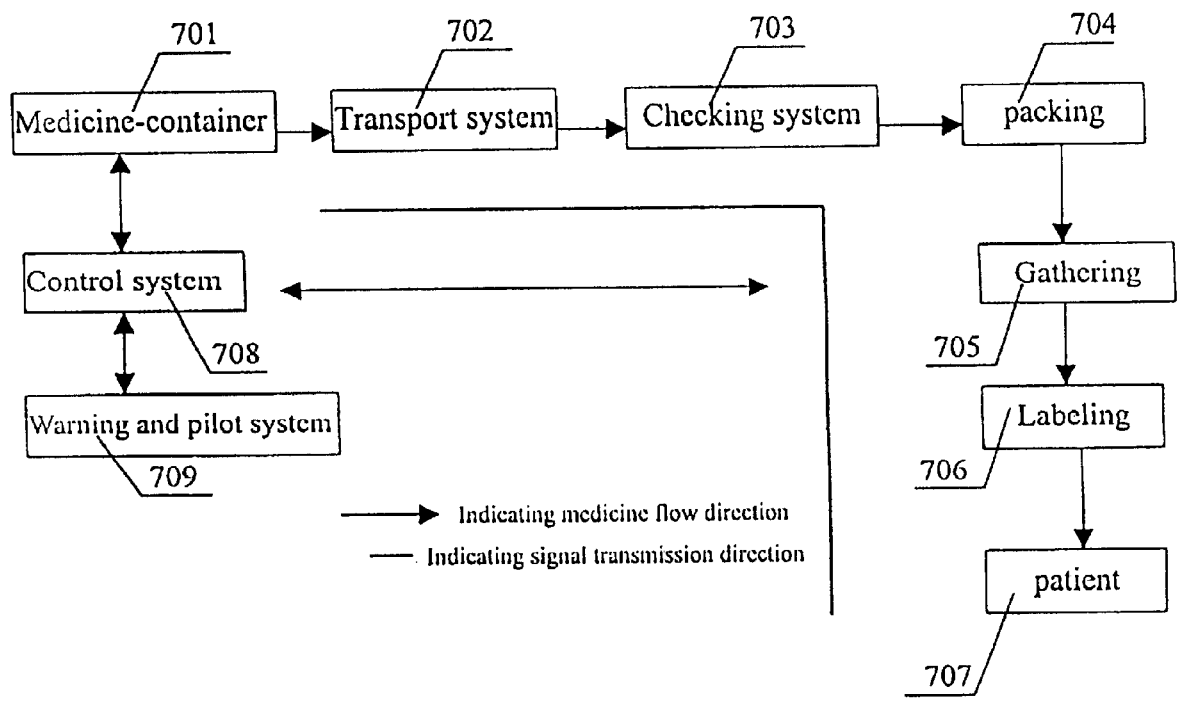
FIG. 7 is the structural view of the composing frame in the example of the invention.

3. The Configuration of the System With Electronic Control Device for Blending of Chinese Herbal Medicine for the Chinese Medicine As shown in FIG. 7, the system with electronic control device for blending of Chinese herbal medicine according to the present invention includes the following parts:

The medicine container 701 for storing drug bags preseted in smallest unit for various drugs, the transmission means 702 conveying the medicine bags, which it transport the medicine to the next place after finishing fetching the medicine bags, the checking system 703 that count and check the medicine bags by a counter, the packing means 704 for prepackaging the medicine bags checked, the final gathering means 705 which can pack the medicine bags packed in the final stage, the mark printing means 706 for printing label on the medicine bags, which print the instruction of medicine taking and dose and paste the label on the package of medicine. Then resultant medicine is passed to the patient 707. The control system 708 is utilized to control whole process. There is alarm means 709 in the system for identifying and warning if any things happen to run down or mistake.

4. Medicine-container

Figure 8:
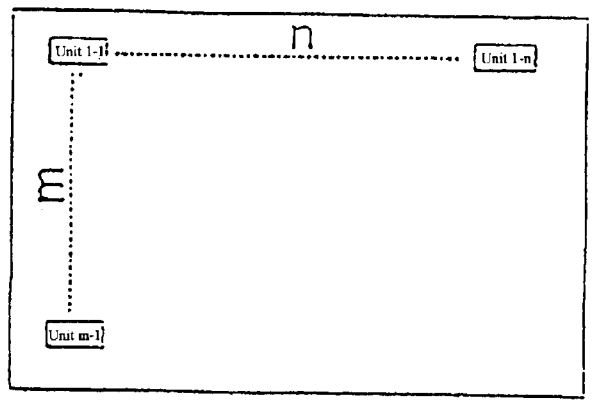
FIG. 8 is the structural view of the medicine container.

The medicine container 701 (seen in FIG. 7) in the system of the present invention includes several units such as mxn units. As shown in FIG. 8, there are m rows and n lists, wherein each unit case can place single kind of medicine and each container can manage mxn kinds of medicines. It is also possible to place one of the frequently used medicines in the two or more unit cases. If i pieces of medicine containers (I>1) are combined, it can at most lodge and manage ixmxn kinds of medicines once. In this way, the computer will determine to take out the medicine from which medicine container and then which unit case according to the prescription. If one prescription of medicine needs to take out the medicine from a few medicine containers, the transmission means between the medicine containers will take out the medicine bags and collect them to one place and pack them.

5. The Automatic Medicine Fetching Means 5.1) The Introduction of the Medicine Fetching Means The so-call medicine fetching in the present invention means that the certain number of drugs are taken out from the drug case, which drugs bags may be a continuous or discontinuous series of medicine bags. If they are continuous units of medicine bags, the medicine fetching means fetch and cut off the series of the medicine bags from the unit case of the container by utilizing the speed difference in the transport of the medicine bags and the intensity difference in the connection and non-connection parts.

5.2) To Extract the Continuous Medicine Bags

Figure 9:
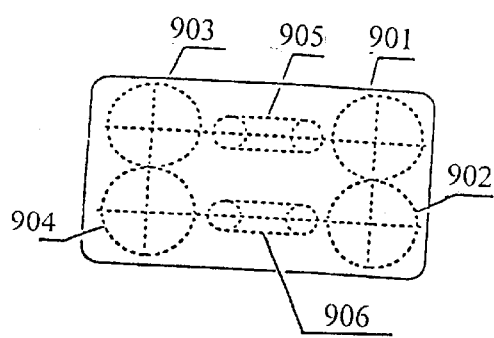
FIG. 9 is a front view of an automatic medicine fetching means used in the invention.
Figure 10:
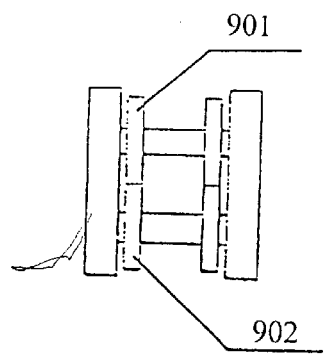
FIG. 10 is a partial side elevational view of the automatic medicine fetching means.
Figure 11:
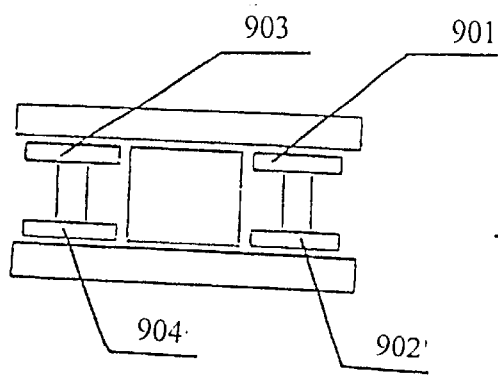
FIG. 11 is a top view of the automatic medicine fetching means.
Figure 13:
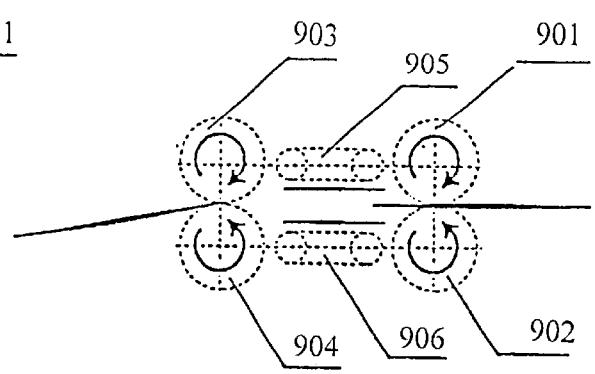
FIG. 12 and FIG. 13 show the process which drug bags are passing the automatic medicine fetching means.
Figure 12:
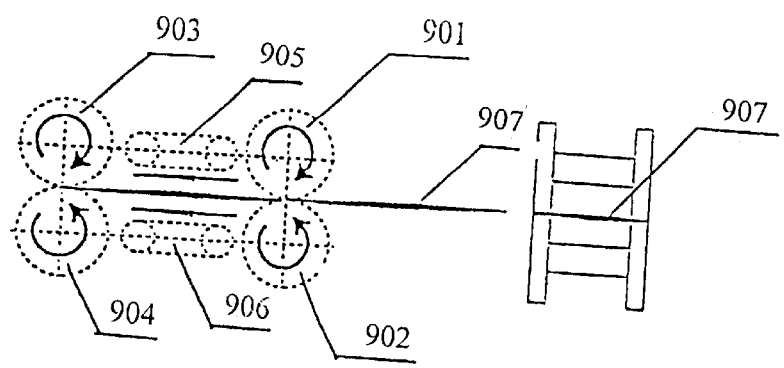
Figure 14:
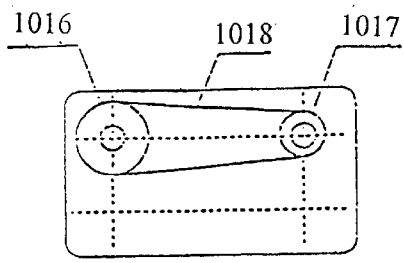
FIG. 14 is the front view of another automatic medicine fetching means used in the invention.
Figure 17:
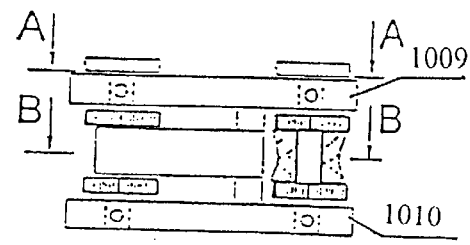
FIG. 17 is the top view of the automatic medicine fetching means.
Figure 15:
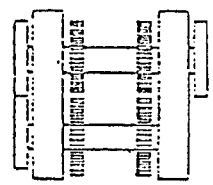
FIG. 15 is the side view of the automatic medicine fetching means.
Figure 18:
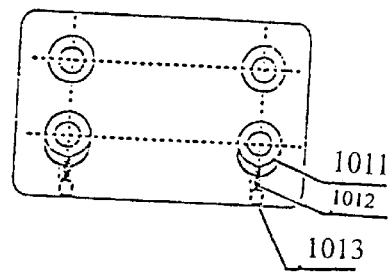
FIG. 18 is a sectional view taken along line A—A of the FIG. 16.
Figure 16:
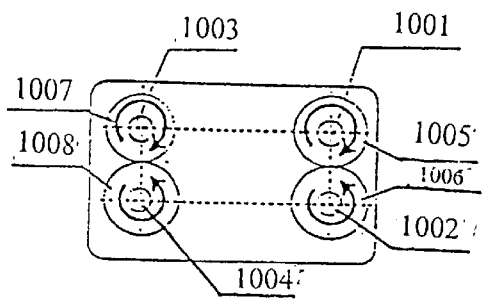
FIG. 16 is the back view of the automatic medicine fetching means.
Figure 19:
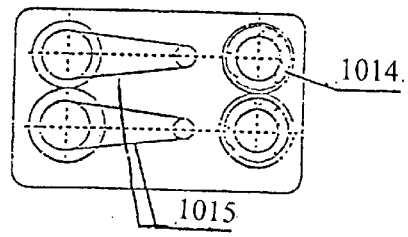
FIG. 19 is a sectional view taken along line B—B of the FIG. 16.

The FIGS. 9–FIG. 11 show the structure of the automatic medicine fetching means. When the chain of the medicine bags move forward, the resultant speed difference can pull apart along cutting line of the medicine bag and separate the medicine bags one by one. This medicine fetching means is applicable in A-A type packing as shown in FIG. 1. In FIGS. 9–11, a pair of medicine bag input wheels 901, 902 and medicine bag output wheels 903, 904 are installed. Between the two pairs of the wheels, the transmission straps 905 and 906 are installed. The distance between the input wheels 901, 902 and output wheels 903, 904 is the length an of a medicine bag (see also FIG. 1). In the Figure, the input wheel 901 and 902 move in an opposite direction. The output wheel 903 and 904 move in an opposite directions either. As shown in FIGS. 12 and 13, the rotate speed of the output wheel 903 and 904 is faster than the rotate speed of the input wheels 901 and 902. As a result of the rotate speed of the output wheel 903 and 904 is faster than the rotate speed of the input wheel 901 and 902, the medicine bags as shown can be pulled apart from the cutting line and delivered accordingly when the medicine bag 907 contact the output wheel 903 and 904 through the wheeling of the input wheel 901 and 902 and entering the transmission strap 905 and 906. The transmission strap 901 and 902 move along the direction of the medicine bag 907 to protect the sloping or jamming of the medicine bag during the transmission.

5.3) Example

FIGS. 14–19 show structure and operation of an example of medicine fetching means in the invention. As shown in Figure, the automatic medicine fetching means comprises four axis 1001–1004 and the four wheels 1005–1008 fixed on the said four axis 1001–1004. The said four axis 1001–1004 are connected to supporting board 1009 and 1010 through bearings. The wheel 1016 and 1017 are fixed on the axis 1001 and 1003 respectively. When the axis 1001 move in the direction of arrow, it will drive the axis 1002 in the arrow direction. At the same time, the wheel 1005 drive the wheel 1016 through the axis 1001. The wheel 1016 will drive the wheel 1017 through the strap 1018. The wheel 1017 will drive the wheel 1007 through the axis 1003. The wheel 1007 will drive the wheel 1004 in the direction of arrow. There are two wheel drums on each axis. For instance, two wheel drums are installed on the axis 1001. There is a line type stripe, which can help clamping the medicine bag. The bolt 1013 presses the bearing through the spring 1012 so that the wheel drum will press the border of the medicine bag. The two straps 1015 can guide the medicine bag. As shown in Figure, the axis 101 and 1002 are provide with the rubber ring 1014 to help bringing in the medicine bag and pulling apart the chain of the medicine bags.

Figure 20:
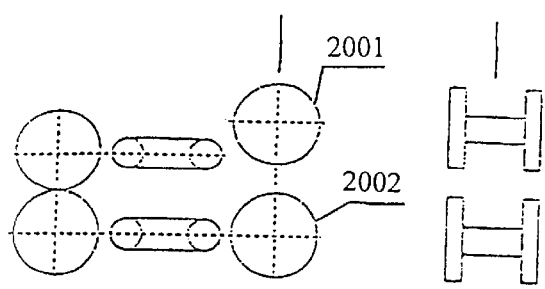
FIGS. 20–21 show the working process of the front wheels in the automatic medicine fetching means in transformation.
Figure 21:
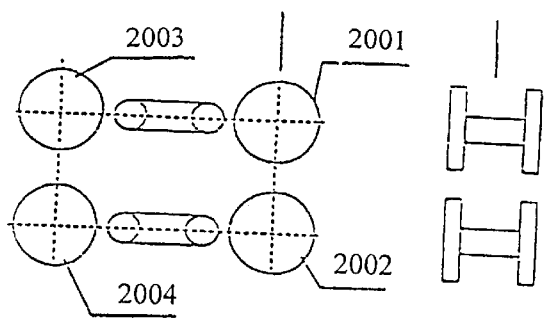

In addition, the input wheel 2001 and 2002 or the two groups of the wheels of input wheels 2001, 2002 and output wheels 2003, 2004 are apart each other before loading the medicine, in another example as shown in FIGS. 20–21. After loading the medicine, the two front wheels are driven close and clamp the medicine bags by a electrical magnetic valve and motor.

5.4) Pressing and Cutting Means

Figure 22:
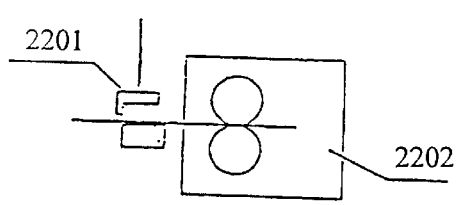
FIG. 22 shows a structure of a pressing and cutting means in the system of the invention.

As shown in the FIG. 22, in the medicine fetching means with pressing and cutting means, The pressing and cutting means 2201 will press and cut the medicine bags on the appropriate position from the bunch of the medicine bags after the medicine delivering means deliver the required quantity of the medicine bags. This medicine-fetching mode is suitable for the packing of the A-A type and A-B type. It can operate by delivering one bag from the transmission means 2202. Then the pressing and cutting means 2201 pull one bag apart. After it fetching out predetermined number of bags, the transmission means will stop.

5.5) The Medicine Fetching Means With Toothed Wheels

Figure 23:
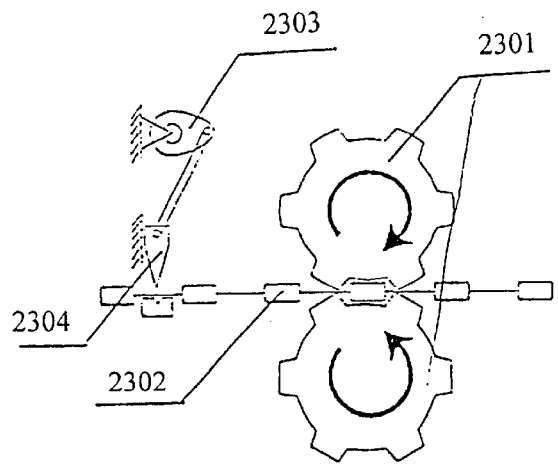
FIG. 23 shows structure of a gear type of medicine fetching means.
Figure 24:
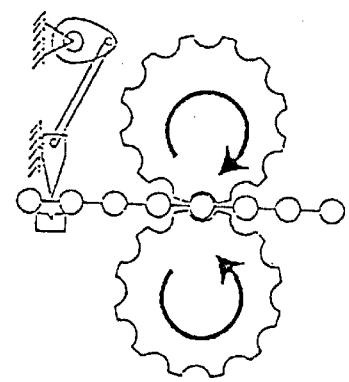
FIG. 24 is a structural view of another toothed wheel type of medicine fetching means.

As shown in the FIGS. 23–24, the medicine fetching means with toothed wheels comprises two toothed wheels 2301 operating in an opposite direction. Whenever it rotates to one unit of angle, it will transport one bag of medicine 2302. By controlling the rotating angle of the toothed wheel 2301, the transported quantity of the medicine can be controlled. In the figure of the sliding means of the cam with connecting bar, the rotate speed of the cam 2303 is same as the rotate speed of the toothed wheel 2301. The knife 2304 on the end of slide means will operate up and down continuously. Whenever the toothed wheel 2301 delivers one pack of medicine, the knife will cut off one pack. Then it can be pulled apart by some other way. This working mode is fit for the A-B type packing. Different kind of tooth shape or different size can be used in different kind of shape and size of medicine packing.

5.6) The Medicine Fetching Means by Valve Control

The medicine fetching means 2503 by valve control is fit for the drug in bulk. The valve can control the falling of the drug one by one. As shown in the FIG. 25, the upper valve 2501 opens first and one pack of drug falls. Then the upper valve 2501 closes and the underside valve 2502 opens. In that way, it finishes fetching one drug bag. The counter can control the fetching quantity of the medicine.

The medicine fetching means by valve control can also be realized in another mode. As shown in the FIG. 26, a cam 2601, a bar 2602 and a slide bar 2603 make up of the sliding means of a cam connecting bar. In the sliding means, the cam 2601 circumrotates around the axes and the slide rod 2603 moves along the arrow direction periodically. When the slide rod 2603 moves to the right side on paper, it pushes open the door cover 2604 and delivers one pack of drug at the same time. When the slide rod 2603 moves to the left direction on paper, the door cover 2604 closes and one pack of drug falls from the medicine container 2605 at the same time. The number of the medicine bags fetched from the funnel storehouse can be controlled by the rotating speed of the cam 2601.

Figure 26:
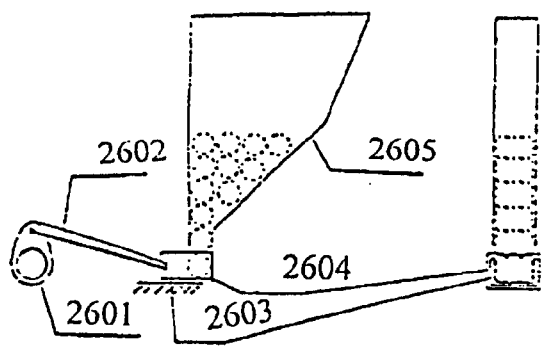
FIG. 26 is a structural view of another valve control of the medicine fetching means.
Figure 27:
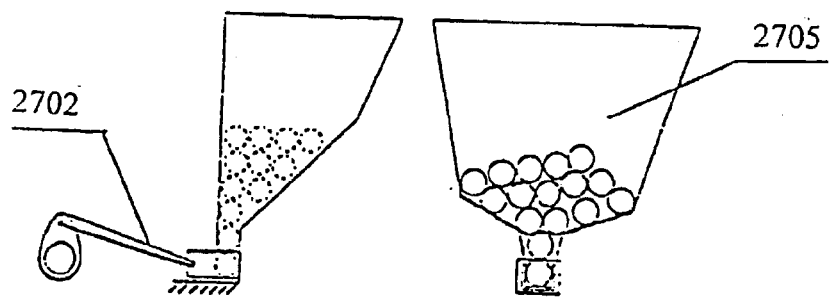
FIG. 27 is a structural view of the third kind of valve control in the medicine fetching means.

The working framework of the FIG. 27 is same as the FIG. 26 on the whole. The former one is fit for the cylinder packing and the bulk packing of the A-C type while the FIG. 27 is applied to the circular bulk packing of the A-C type.

6. Guide Track

Figure 28:
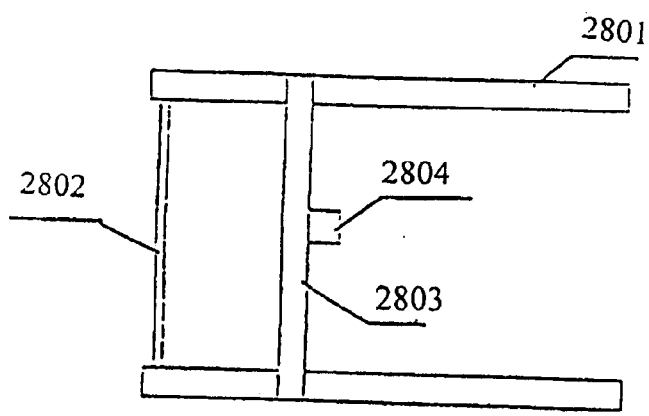
FIG. 28 is a structural view of the guiding track, which can seek the location of the unit.
Figure 29:
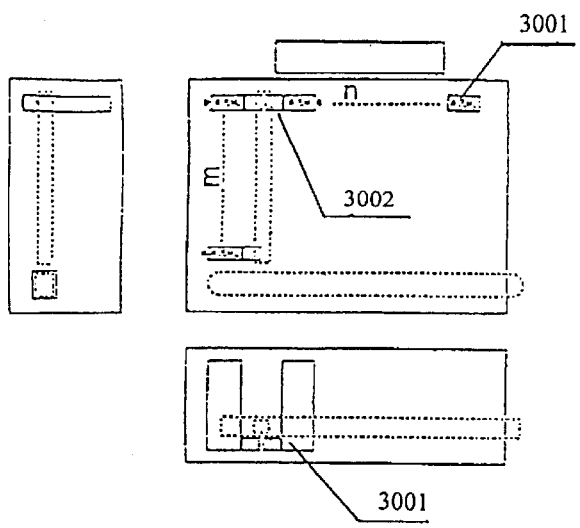
FIG. 29 is a structural view of embodiment that each unit is installed with one medicine fetching means separately.

In the method and system of the present invention, it will need a servo means to let the medicine fetching means move to the selected unit case, if the number of the medicine fetching means is less than the quantity of the unit cases, which requires that several cases share the same medicine fetching means. As shown in the FIG. 28, two axes X spindles 2801 can be installed on both the upper side and the lower side of the medicine container. The two axes X spindles 2801 are connected through the axis Y linkage spindle 2802 so that they can synchronize. When searching a unit case, the axis Z medicine fetching means 2804 which is installed for final movement on the axis Z (out of the plane of FIG. 28) initially moves up or down along the axis Y element 2803, while the axis Y element 2803 perpendicular to the axis X spindles 2801 moves left and right. When the medicine fetching means 2804 is searching the unit case, axis Y element 2803 locates its correspond position on axis X spindles 2801 firstly, then the axis Z fetching means 2804 move up and down along axis Y element 2803, finally, it will take out medicine bag and pull it apart from the drug box of the unit case by moving along the direction of the axis Z. In the application, it can be a system with two axes Y elements or one axis Y element and one axis Z fetching means, or a guide track system with an axis X element, an axis Y element and an axis Z fetching means.

7. Warning Means

The system according to the present invention is provided with a warning means, which is used to generate warning signal when medicine are used up or misplace medicine. There are several kinds of warning means.

7.1) Signal Lamp

In this alarm means, each medicine unit is equipped with a signal lamp. After fetching the medicine over, the signal lamp will light. When append the medicine, the bar-code reader will read the bar code on the box of medicine. If the medicine is compatible with the medicine unit, the signal lamp begins flickering. After loading the medicine, it will read the bar code on the cover of the unit and turn off. In other words, it will read the bar code on the medicine box and the cover of the unit separately so as to prevent from wrong packing.

7.2) Indicating Board

After the medicine in a unit has been fetched out, the indicting board will display the name of the medicine and its position. When loading medicine, it will read the bar code on the medicine box. The indicating board will notify if the medicine has been loaded correctly. If correct, the medicine will be loaded.

7.3) Electrical Lock

When the medicine in a unit has all been fetched, the system will alarm. When loading medicine, it will read the bar code on the medicine box. If correct, the electrical lock of the unit will open. Otherwise, the electrical lock of the opposite unit will open. In this design, it can ensure that the medicine will not be loaded into other unit.

8. Example 1

In the example of the application of the invention:
1) Every unit uses one medicine fetching means. In this way, it dose not Need guide and locating.
2) The medicine fetching means adopts the structure as shown in the FIGS. 12 and 13;
3) The packing structure can be as the box shape of the A-A type and A-B Type.
4) The warning means can be an indicating board, an Indicator light or an electrical lock. If it is not an electrical lock, the lock has structure as shown in the FIGS. 30–32.

Figure 30:
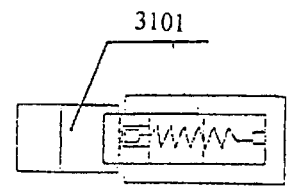
FIGS. 30–32 are structural views of the door lock of the unit case.
Figure 31:
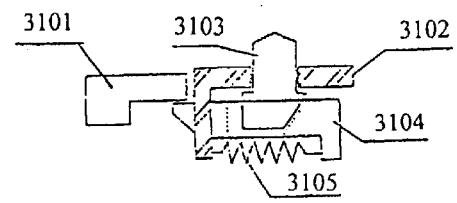
Figure 32:
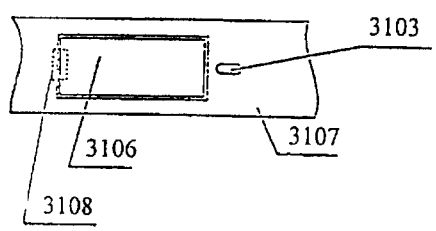
Figure 33:
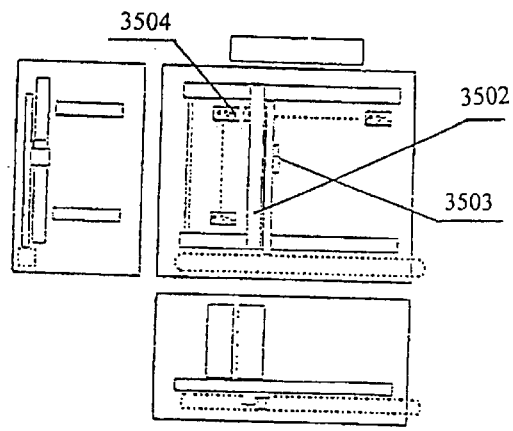
FIG. 33 is a structural view of an example sharing the same medicine fetching means.

As shown in the FIGS. 30–32, the piece 3101 is fixed on the door. The pieces 3102, 3103, 3104, 3105 are fixed on the bracket 3107. When pressing the button 3103, the button 3103 pushes the button 3104 to the right. Button 3104 is apart from piece 3101 at one time. The door 3106 will flick around the hinge 3108 and the door is open. By pushing the door to the opposite direction, the door will look.

Figure 25:
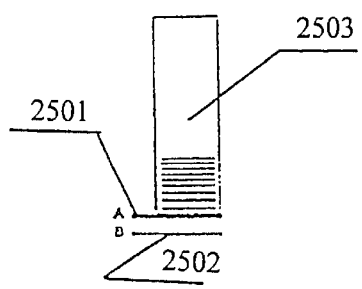
FIG. 25 is a structural sketch of a valve control type of the medicine fetching means.
Figure 25:
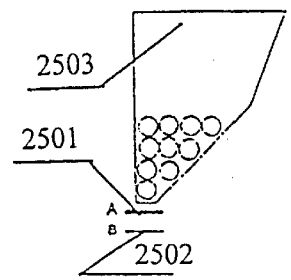

The above structure fits the structure of the medicine fetching means as shown in the FIG. 25 and the medicine packing in A-C type shown in FIG. 6. The warning means can use indicating board.

9. Example 2

1) All Medicine Units Share One Medicine Fetching Means

In this system, the axis Z automatic medicine fetching means 3503 is fixed. It can be delivered to any unit 3504 in any position through the guide track moving in three directions. The supplying bucket is installed onto the axis Y element 3502. After the medicine fetching means 3503 finishes fetching some medicine, the medicine bags will be deliver to the supplying bucket and fall into the transmission means. The example fits for the medicine of the A-A type packing and the medicine of A-B type packing, if the medicine fetching means shown in the FIGS. 9–11 and FIG. 20 are used. The warning means can be one of the three types of the abovementioned structure. If non-electrical lock is used, the switch of the door can employ the structure as shown in the FIGS. 30–32.

2) Guide Means

Figure 34:
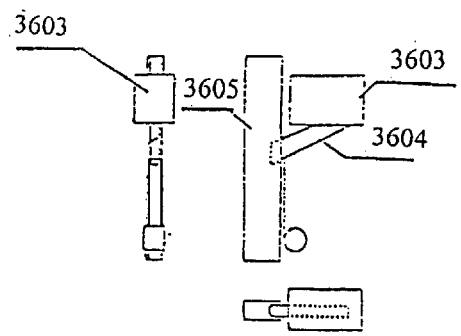
FIG. 34 is a structural view of the supply means used in the present invention.
Figure 35:
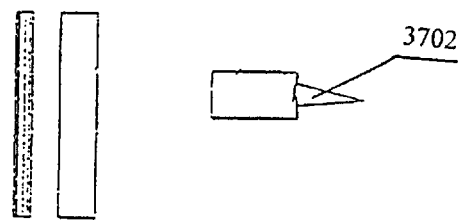
FIG. 35 is a structural view of the supply means in more detail.

In the guide means shown in the FIGS. 34–35, the medicine will fall onto the transmission strap means through the material guiding channel 3604 after the medicine is taken out by the medicine fetching means 3603. Antileak patch can flex up and down along the material guiding channel to protect the medicine leak out of the placket of the supplying bucket. In the FIG. 35, the two rubber patches 3702 are installed on the two sides of the supply bucket placket. The center joint laps over a bit so that the material-guiding channel can move up and down in the interspace. The two patches in other position will close to protect leakage of the medicine.

Figure 36:
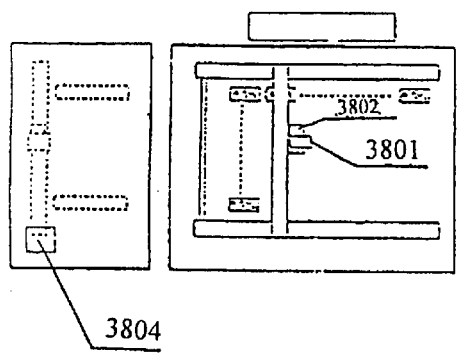
FIG. 36 shows application of the supply means in the system.

In addition, the supply means can be the material-feeding box 3801 attached to the medicine fetching means. Whenever the medicine fetching means 3802 take out one pack of medicine, it will deliver the medicine to the said material feeding box 3801. After fetching one pack of medicine, the feeding box 3801 will be delivered to the exit 3804 on the lower right corner of the cabinet as shown in the FIG. 36.

3) Transmission Means

Figure 37:
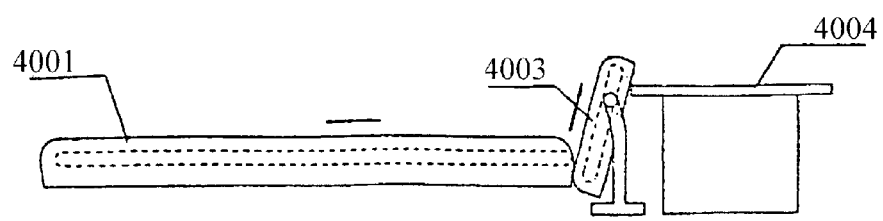
FIG. 37 is a structural view of a transmission means.

The transmission means shown in the FIG. 37 includes the horizontal transmission strap 4001 which takes over the medicine bags by the medicine fetching means, the worktable 4004 for the apothecaries and patients, the lifting strap 4003 which is connected between the end of the horizontal transmission strap and the worktable. A baffle is installed on both sides of the lifting strap to prevent the medicine off the track. The medicine fetching means will transmit the medicine bags to the horizontal transmission strap through the guide means and deliver them to the worktable by the slanting lifting strap.

Figure 38:
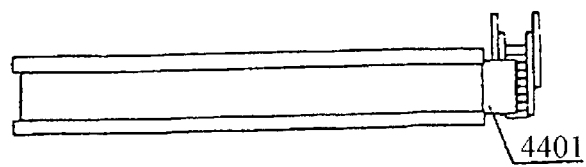
FIG. 38 is a structural view of another transmission means.
Figure 39:
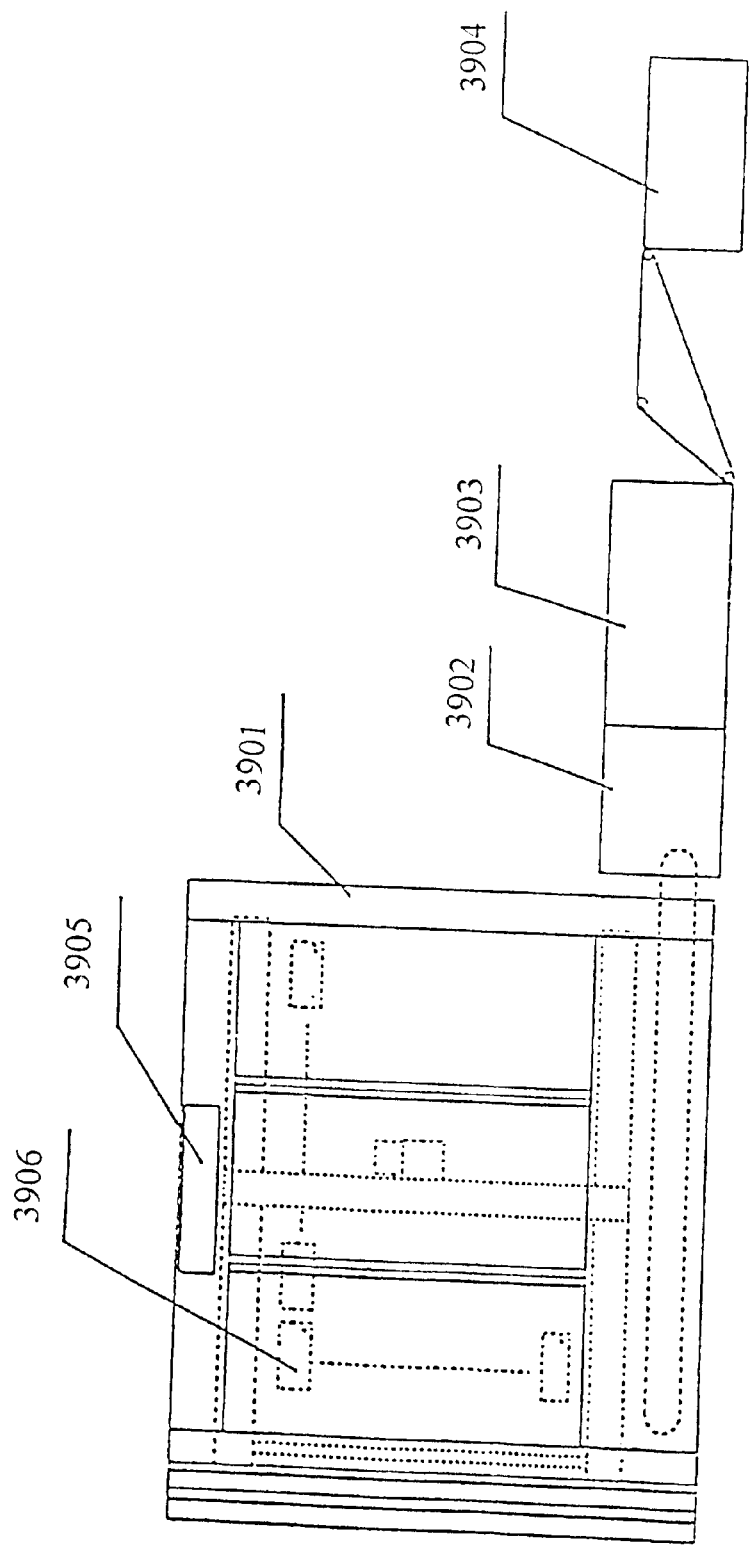
Figure 40:
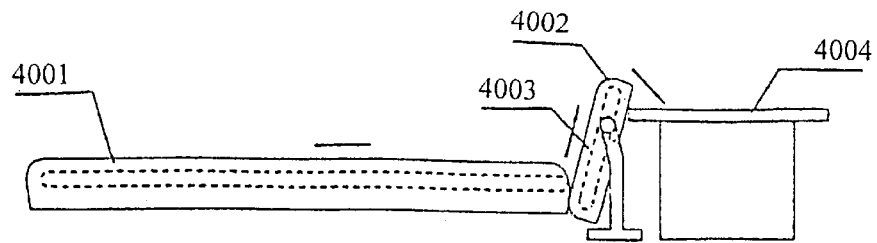
Figure 41:
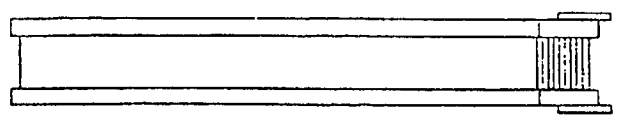
Figure 42:
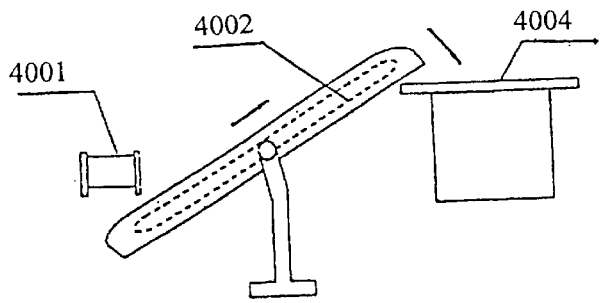
Figure 43:
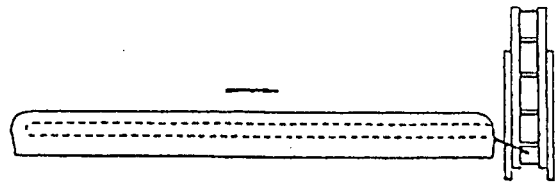
Figure 44:
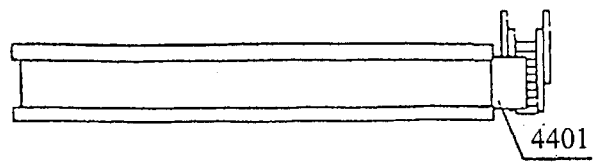

In the example of the transmission means shown in the FIG. 38, a guide patch 4401 is installed between the horizontal transmission strap and the lifting strap. It is usable for the condition of which both are far apart.

What is claimed is:

1. A system for blending of Chinese herbal medicines comprising:

one or more medicine-containers consisting of a number of storage units for storing different sorts of Chinese medicines, a fetching means for fetching a certain quantity of medicine bags from the storage unit, a transmitting and guiding means for putting medicine bags from the fetching means onto a conveyer belt, a warning means for identifying and warning if certain medicine bags run down or are misplaced, a control device for controlling said fetching, transmitting and guiding, and warning means according to a prescription for blended Chinese herbal medicines, a checking system for counting the quantity of the medicine fetched out by said fetching means, a packing means used for packing the medicine bags checked, a final gathering means used for gathering the medicine bags packed, and a labeling means for printing a label on medicine bags packed.

2. The system as claimed in claim 1 wherein every storage unit consists of one fetching means such that each said fetching means in each unit is provided with a guiding means which is used for conveying the medicine bags onto conveying straps.

3. The system as claimed in claim 1:

wherein all of the storage units share one fetching means; and wherein the medicine container further comprises a servo-mechanism which can drive said medicine fetching means to move to any storage unit predetermined along a guide track according to an instruction from a computer.

4. The system as claimed in claim 3:

wherein said guide track can be an upside or downside guide track;

wherein said servo-mechanism comprises a vertical guide track which can shift horizontally along the upside or downside guide track; and wherein said medicine fetching means can move up and down along said vertical guide track.

5. The system as claimed in claim 4 wherein said servo-mechanism comprises a means which can drive said medicine fetching means to advance and retreat in a Z direction and pull out the medicine bags from the storage unit.

6. The system as claimed in claim 4:

wherein said guiding means is installed on said medicine fetching means shared;

wherein said guiding means is made up of the vertical frame with a placket and an antileak patch with a bit superposition on the two sides of the placket; and wherein said medicine fetching means moves up and down along two sides of the antileak patch so as to fetch the medicine bags and drop said medicine bags down on the conveying strap.

7. The system as claimed in claim 4:

wherein said guiding means includes an upright supply bucket with a side channel on a side of the medicine fetching means shared, and a transport groove between the bottom of said medicine fetching means and the supply bucket; and wherein from the connection of the supply bucket to the placket of said upright supply bucket, there is an antileak patch which can move up and down along with the transport groove for protecting the leaking of the drug from an opening of the supply bucket.

8. The system as claimed in claim 4:

wherein said guiding means is a small box that is connected with said medicine fetching means; and wherein a pack of the drug is delivered to the small box and the medicine fetching means will delivery said small box to an exit of a tank after fetching one set pack of the medicine.

9. The system as claimed in claim 1:

wherein said warning means includes a bar-code reader, and a signal lamp on every unit storing the medicine containers;

wherein the signal lamp for an empty medicine container will light after the medicine runs out of stock in that medicine container, wherein the bar-code reader will read a bar code on the medicine container when the medicine container is positioned in the unit, and the said signal lamp will flicker if the medicine indicated by the bar code is the same as the medicine desired for the unit; and wherein after the drugs are loaded, the bar code reader also reads a bar code of a cover of the unit so that if the medicine read from the medicine container the same and hence the medicine container is loaded correctly, the signal lamp will turn off.

10. The system as claimed in claim 1:

wherein said warning means comprises the bar-code reader and an indicator such that after the medicine in a certain unit has been fetched out, the indicator displays the drug's name and place; and wherein when loading the medicine container, the bar-code reader will read a bar code on the medicine container and detect if the medicine therein is the right medicine for that unit.

11. A system for blending of Chinese herbal medicines comprising:

one or more medicine-containers consisting of a number of storage units for storing different sorts of Chinese medicines, a fetching means for fetching a certain quantity of medicine bags from the storage unit, a transmitting and guiding means for putting medicine bags from the fetching means onto a conveyer belt, a warning means for identifying and warning if certain medicine bags run down or are misplaced, a control device for controlling said fetching, transmitting and guiding, and warning means according to a prescription for blended Chinese herbal medicines, wherein said medicine fetching means comprises a first valve, a second valve, and a control system, said control system controlling said first and second valves such that said first valve will open and deliver the certain quantity of medicine bags and then close, whereby in the end, the second valve will open and the drugs are fetched.

12. The system as claimed in claim 11 wherein every storage unit consists of one fetching means such that each said fetching means in each unit is provided with a guiding means which is used for conveying the medicine bags onto conveying straps.

13. The system as claimed in claim 11:

wherein all of the storage units share one fetching means; and wherein the medicine container further comprises a servo-mechanism which can drive said medicine fetching means to move to any storage unit predetermined along a guide track according to an instruction from a computer.

14. The system as claimed in claim 13:

wherein said guide track can be an upside or downside guide track;

wherein said servo-mechanism comprises a vertical guide track which can shift horizontally along the upside or downside guide track; and wherein said medicine fetching means can move up and down along said vertical guide track.

15. The system as claimed in claim 13 wherein said servo-mechanism comprises a means which can drive said medicine fetching means to advance and retreat in a Z direction and pull out the medicine bags from the storage unit.

16. The system as claimed in claim 13:

wherein said guiding means is installed on said medicine fetching means shared;

wherein said guiding means is made up of the vertical frame with a placket and an antileak patch with a bit superposition on the two sides of the placket; and wherein said medicine fetching means moves up and down along two sides of the antileak patch so as to fetch the medicine bags and drop said medicine bags down on the conveying strap.

17. The system as claimed in claim 13:

wherein said guiding means includes an upright supply bucket with a side channel on a side of the medicine fetching means shared, and a transport groove between the bottom of said medicine fetching means and the supply bucket; and wherein from the connection of the supply bucket to the placket of said upright supply bucket, there is an antileak patch which can move up and down along with the transport groove for protecting the leaking of the drug from an opening of the supply bucket.

18. The system as claimed in claim 13:

wherein said guiding means is a small box that is connected with said medicine fetching means; and wherein a pack of the drug is delivered to the small box and the medicine fetching means will delivery said small box to an exit of a tank after fetching one set pack of the medicine.

19. The system as claimed in claim 11:

wherein said warning means includes a bar-code reader, and a signal lamp on every unit storing the medicine;

wherein the signal lamp for an empty medicine container will light after the medicine runs out of stock in that medicine container, wherein the bar-code reader will read a bar code on the medicine container when the medicine is positioned in the unit, and the said signal lamp will flicker if the medicine indicated by the bar code is the same as the medicine desired for the unit; and wherein after the drugs are loaded, the bar code reader also reads a bar code of a cover of the unit so that if the medicine read from the medicine container the same and hence the medicine container is loaded correctly, the signal lamp will turn off.

20. The system as claimed in claim 11:

wherein said warning means comprises the bar-code reader and an indicator such that after the medicine in a certain unit has been fetched out, the indicator displays the drug's name and place; and wherein when loading the medicine container, the bar-code reader will read a bar code on the medicine container and detect if the medicine therein is the right medicine for that unit.

21. A system for blending of Chinese herbal medicines comprising:

one or more medicine-containers consisting of a number of storage units for storing different sorts of Chinese medicines, a fetching means for fetching a certain quantity of medicine bags from the storage unit, a transmitting and guiding means for putting medicine bags from the fetching means onto a conveyer belt, a warning means for identifying and warning if certain medicine bags run down or are misplaced, a control device for controlling said fetching, transmitting and guiding, and warning means according to a prescription for blended Chinese herbal medicines, wherein said medicine fetching means comprises paired input wheels and paired output wheels which engage the medicine bag, the conveying belt being between both pairs for conveying the medicine bags along a movement direction of the bags, wherein a length between said input and the output wheels is equal to length "a" of the medicine bags, and wherein a rotational speed of said input wheels is slower than a rotational speed of the output wheels.

22. The system as claimed in claim 21 wherein every storage unit consists of one fetching means such that each said fetching means in each unit is provided with a guiding means which is used for conveying the medicine bags onto conveying straps.

23. The system as claimed in claim 21:

wherein all of the storage units share one fetching means; and wherein the medicine container further comprises a servo-mechanism which can drive said medicine fetching means to move to any storage unit predetermined along a guide track according to an instruction from a computer.

24. The system as claimed in claim 23:

wherein said guide track can be an upside or downside guide track;

wherein said servo-mechanism comprises a vertical guide track which can shift horizontally along the upside or downside guide track; and wherein said medicine fetching means can move up and down along said vertical guide track.

25. The system as claimed in claim 24 wherein said servo-mechanism comprises a means which can drive said medicine fetching means to advance and retreat in a Z direction and pull out the medicine bags from the storage unit.

26. The system as claimed in claim 24:

wherein said guiding means is installed on said medicine fetching means shared;

wherein said guiding means is made up of the vertical frame with a placket and an antileak patch with a bit superposition on the two sides of the placket; and wherein said medicine fetching means moves up and down along two sides of the antileak patch so as to fetch the medicine bags and drop said medicine bags down on the conveying strap.

27. The system as claimed in claim 24:

wherein said guiding means includes an upright supply bucket with a side channel on a side of the medicine fetching means shared, and a transport groove between the bottom of said medicine fetching means and the supply bucket; and wherein from the connection of the supply bucket to the placket of said upright supply bucket, there is an antileak patch which can move up and down along with the transport groove for protecting the leaking of the drug from an opening of the supply bucket.

28. The system as claimed in claim 24:

wherein said guiding means is a small box that is connected with said medicine fetching means; and wherein a pack of the drug is delivered to the small box and the medicine fetching means will delivery said small box to an exit of a tank after fetching one set pack of the medicine.

29. The system as claimed in claim 21:

wherein said warning means includes a bar-code reader, and a signal lamp on every unit storing the medicine;

wherein the signal lamp for an empty medicine container will light after the medicine runs out of stock in that medicine container, wherein the bar-code reader will read a bar code on the medicine container when the medicine is positioned in the unit, and the said signal lamp will flicker if the medicine indicated by the bar code is the same as the medicine desired for the unit; and wherein after the drugs are loaded, the bar code reader also reads a bar code of a cover of the unit so that if the medicine read from the medicine container the same and hence the medicine container is loaded correctly, the signal lamp will turn off.

30. The system as claimed in claim 21:

wherein said warning means comprises the bar-code reader and an indicator such that after the medicine in a certain unit has been fetched out, the indicator displays the drug's name and place; and wherein when loading the medicine container, the bar-code reader will read a bar code on the medicine container and detect if the medicine therein is the right medicine for that unit.

31. A system for blending of Chinese herbal medicines comprising:

one or more medicine-containers consisting of a number of storage units for storing different sorts of Chinese medicines, a fetching means for fetching a certain quantity of medicine bags from the storage unit, a transmitting and guiding means for putting medicine bags from the fetching means onto a conveyer belt, a warning means for identifying and warning if certain medicine bags run down or are misplaced, a control device for controlling said fetching, transmitting and guiding, and warning means according to a prescription for blended Chinese herbal medicines, wherein the medicine fetching means comprises two gears moving in opposite directions and wherein the two gears can deliver one pack of drug whenever the two gears turn into a preselected angle, whereby the medicine fetching means can deliver a certain quantity of the drugs by controlling a rotating angle of the two gears.

32. The system as claimed in claim 31 wherein every storage unit consists of one fetching means such that each said fetching means in each unit is provided with a guiding means which is used for conveying the medicine bags onto conveying straps.

33. The system as claimed in claim 31:

wherein all of the storage units share one fetching means; and wherein the medicine container further comprises a servo-mechanism which can drive said medicine fetching means to move to any storage unit predetermined along a guide track according to an instruction from a computer.

34. The system as claimed in claim 33:

wherein said guide track can be an upside or downside guide track;

wherein said servo-mechanism comprises a vertical guide track which can shift horizontally along the upside or downside guide track; and wherein said medicine fetching means can move up and down along said vertical guide track.

35. The system as claimed in claim 34 wherein said servo-mechanism comprises a means which can drive said medicine fetching means to advance and retreat in a Z direction and pull out the medicine bags from the storage unit.

36. The system as claimed in claim 34:

wherein said guiding means is installed on said medicine fetching means shared;

wherein said guiding means is made up of the vertical frame with a placket and an antileak patch with a bit superposition on the two sides of the placket; and wherein said medicine fetching means moves up and down along two sides of the antileak patch so as to fetch the medicine bags and drop said medicine bags down on the conveying strap.

37. The system as claimed in claim 34:

wherein said guiding means includes an upright supply bucket with a side channel on a side of the medicine fetching means shared, and a transport groove between the bottom of said medicine fetching means and the supply bucket; and wherein from the connection of the supply bucket to the placket of said upright supply bucket, there is an antileak patch which can move up and down along with the transport groove for protecting the leaking of the drug from an opening of the supply bucket.

38. The system as claimed in claim 34:

wherein said guiding means is a small box that is connected with said medicine fetching means; and wherein a pack of the drug is delivered to the small box and the medicine fetching means will delivery said small box to an exit of a tank after fetching one set pack of the medicine.

39. The system as claimed in claim 31:

wherein said warning means includes a bar-code reader, and a signal lamp on every unit storing the medicine;

wherein the signal lamp for an empty medicine container will light after the medicine runs out of stock in that medicine container, wherein the bar-code reader will read a bar code on the medicine container when the medicine is positioned in the unit, and the said signal lamp will flicker if the medicine indicated by the bar code is the same as the medicine desired for the unit; and wherein after the drugs are loaded, the bar code reader also reads a bar code of a cover of the unit so that if the medicine read from the medicine container the same and hence the medicine container is loaded correctly, the signal lamp will turn off.

40. The system as claimed in claim 31:

wherein said warning means comprises the bar-code reader and an indicator such that after the medicine in a certain unit has been fetched out, the indicator displays the drug's name and place; and wherein when loading the medicine container, the bar-code reader will read a bar code on the medicine container and detect if the medicine therein is the right medicine for that unit.

* * * * *